United States Patent
Gerberding

(10) Patent No.: US 6,689,144 B2
(45) Date of Patent: Feb. 10, 2004

(54) RAPID EXCHANGE CATHETER AND METHODS FOR DELIVERY OF VASO-OCCLUSIVE DEVICES

(75) Inventor: Brent C Gerberding, Alameda, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/071,454

(22) Filed: Feb. 8, 2002

(65) Prior Publication Data

US 2003/0153934 A1 Aug. 14, 2003

(51) Int. Cl.[7] ............................................. A61B 17/04
(52) U.S. Cl. ....................................................... 606/157
(58) Field of Search ................................ 606/151, 157, 606/153, 155, 156

(56) References Cited

U.S. PATENT DOCUMENTS

| | | | | |
|---|---|---|---|---|
| 31,272 | A | * | 1/1861 | Pevsner ........................ 604/28 |
| 4,468,224 | A | * | 8/1984 | Enzmann et al. ........... 604/247 |
| 4,994,069 | A | | 2/1991 | Ritchart et al. |
| 5,135,535 | A | | 8/1992 | Kramer |
| 5,154,725 | A | | 10/1992 | Leopold |
| 5,232,445 | A | * | 8/1993 | Bonzel ......................... 606/94 |
| 5,683,410 | A | * | 11/1997 | Samson ....................... 606/194 |
| 5,976,107 | A | * | 11/1999 | Mertens et al. ......... 604/164.13 |
| 6,077,291 | A | * | 6/2000 | Das ............................. 606/213 |
| 6,083,232 | A | | 7/2000 | Cox |
| 6,159,225 | A | * | 12/2000 | Makower .................... 606/155 |
| 6,165,167 | A | | 12/2000 | Delaloye |
| 6,273,899 | B1 | * | 8/2001 | Kramer ....................... 606/194 |
| 6,440,097 | B1 | * | 8/2002 | Kupiecki .................... 606/194 |
| 6,503,223 | B1 | * | 1/2003 | Sekido et al. ............. 604/96.01 |

FOREIGN PATENT DOCUMENTS

WO          WO 99/44667          9/1999

* cited by examiner

*Primary Examiner*—Michael J. Milano
*Assistant Examiner*—Victor Nguyen
(74) *Attorney, Agent, or Firm*—Bingham McCutchen LLP

(57) ABSTRACT

A rapid exchange catheter having a control valve spaced proximal the distal tip of the catheter. The control valve directing a guidewire out of the lumen catheter through an opening in the side wall of the catheter while allowing passage of a vaso-occlusive device through the lumen of the catheter while preventing the vaso-occlusive device from exiting through the opening.

21 Claims, 4 Drawing Sheets

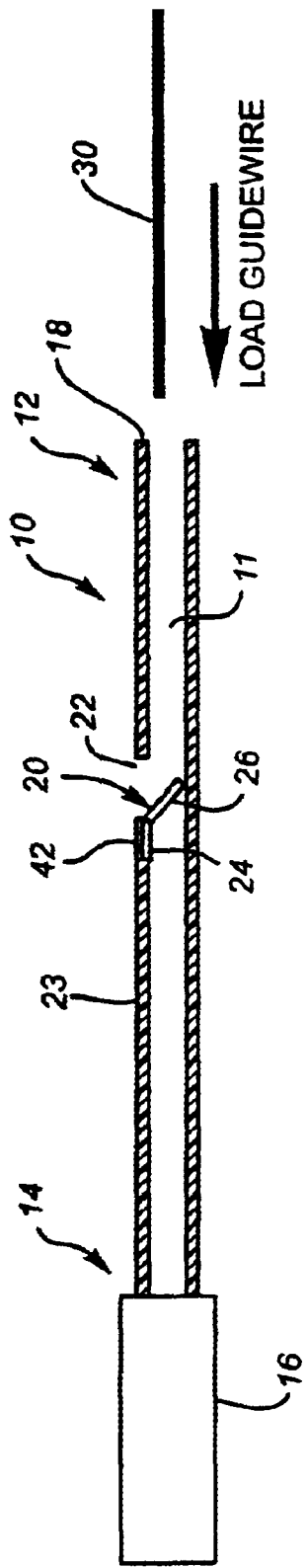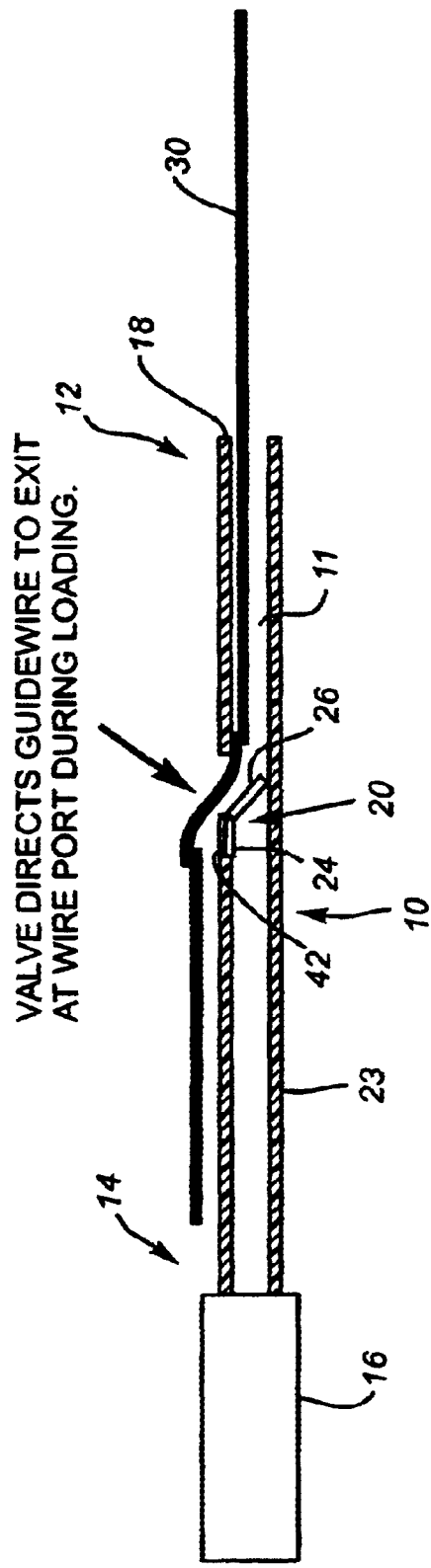

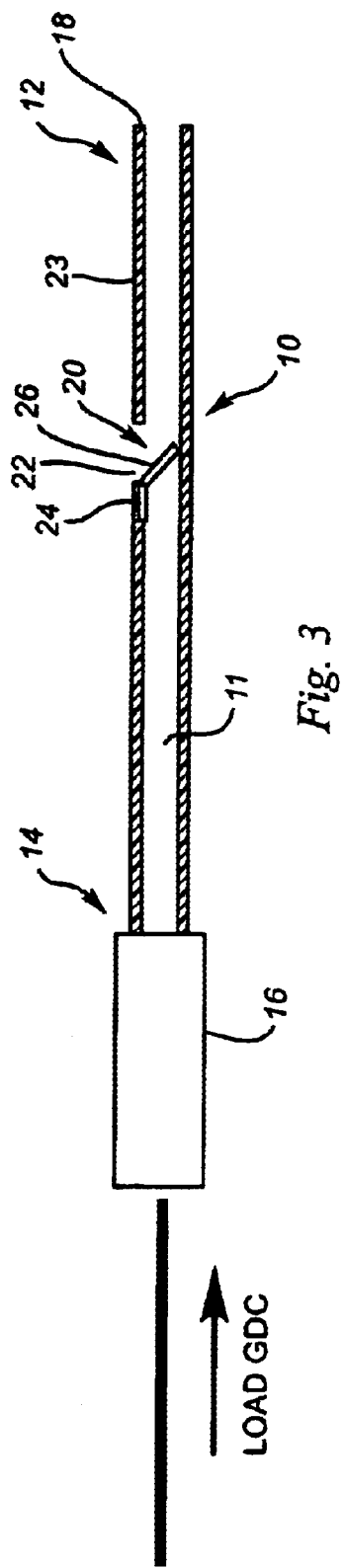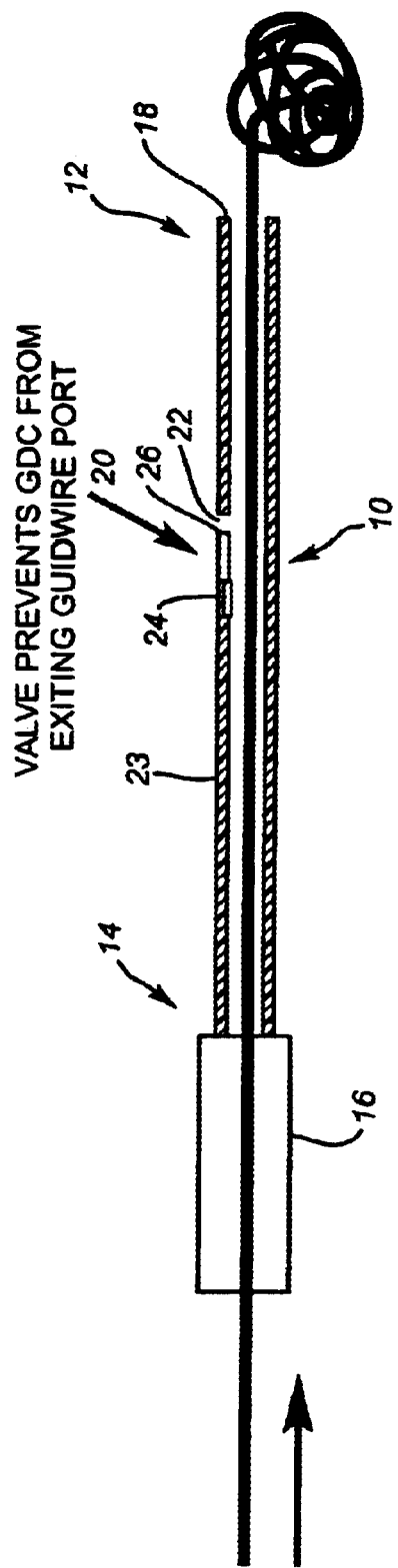

RAPID EXCHANGE CATHETER AND METHODS FOR DELIVERY OF VASO-OCCLUSIVE DEVICES

BACKGROUND OF THE INVENTION

The field of the invention relates generally to vascular catheters.

Vascular catheters are surgical implements used to deliver, among other devices, vaso-occlusive devices. Vaso-occlusive devices are used to occlude sites in the human vasculature, such as an aneurysm. Typically, the catheter is guided into position through the patient's vasculature using a guidewire. Once the guidewire is guided to the desired site in the vasculature, the catheter is advanced over the guidewire so that the distal end of the catheter opens to the desired site in the vasculature.

With the use of such over the wire catheters, the guidewire needs to extend a sufficient distance outside of the patient's body to enable the catheter to be threaded onto the guidewire without disturbing the positioning of the guidewire. Typically, a guidewire extension is attached to the proximal end of the guidewire in order to provide the additional length necessary to thread the guidewire into the catheter. The typical catheter ranges in length from 120 cm to 160 cm. Therefore, the guidewire extension can be quite long and awkward to manipulate as it extends outside the patient's body. This may require an additional medical assistant to solely monitor or manipulate the guidewire.

An alternative catheter design is the "monorail" or rapid exchange variant of the over the wire system. The rapid exchange or "monorail" catheter has a first lumen running the length of the catheter and a second shorter lumen located at one end. The guidewire is threaded through the second shorter lumen at the end of the catheter, which acts as the "monorail." Because the lumen is quite short, only a short length of guidewire needs to extend outside the patient's body, thus allowing a single operator to guide the catheter over the wire without the need of an assistant.

A variation of this rapid exchange design is to provide a slit or opening in the wall of a single lumen catheter a short distance from the distal end of the catheter. The guidewire then passes through the lumen of the catheter and out this slit or opening, such that only a small portion of the catheter is over the guidewire. While this design allows for easy exchange of the guidewire in the catheter, it is not desirable for delivery of vaso-occlusive devices because the vaso-occlusive device may exit out of the slit or opening instead of through the lumen of the catheter, resulting in improper placement of the vaso-occlusive device.

Thus, there is a need for an improved rapid exchange single lumen catheter that can deliver vaso-occlusive devices.

SUMMARY OF THE INVENTION

To these ends, the present rapid exchange or "monorail" catheter includes a control valve adjacent to an opening in the side wall of the catheter at its distal end, which allows placement of the catheter over a guidewire while at the same time allows for delivery of vaso-occlusive devices through the lumen of the catheter. As the catheter is loaded on the guidewire, the control valve directs the guidewire out of the lumen of the catheter. Once the catheter is positioned at the appropriate site in the vasculature, the guidewire is removed and a vaso-occlusive device is loaded into the catheter. As the vaso-occlusive device is pushed through the catheter to the desired site, the vaso-occlusive device forces the control valve to close, which prevents the vaso-occlusive device from exiting through the opening in the side of the rapid exchange catheter.

Other and further aspects and features of the invention will be evident from reading the following detailed description of the drawings, which is intended to illustrate, but not limit, the invention. The invention resides as well in sub-combinations of the features and steps described.

BRIEF DESCRIPTION OF THE DRAWINGS

The drawings illustrate the design and utility of preferred embodiments of the present invention, in which similar elements are referred to by common reference numerals.

FIG. 1 is a side elevational view of an embodiment of a catheter with a distally located control valve just prior to loading the catheter onto the guidewire;

FIG. 2 is a side elevational view of the embodiment of FIG. 1 with the catheter loaded onto the guidewire;

FIG. 3 is side elevational view of the embodiment of FIG. 1 after the guidewire has been removed and prior to loading a vaso-occlusive device into the catheter;

FIG. 4 is a side elevational view of the embodiment of FIG. 1 with the control valve preventing the vaso-occlusive device from exiting the catheter through the guidewire port;

DETAILED DESCRIPTION OF THE PREFERRED EMBODIMENTS

Figure 5A:
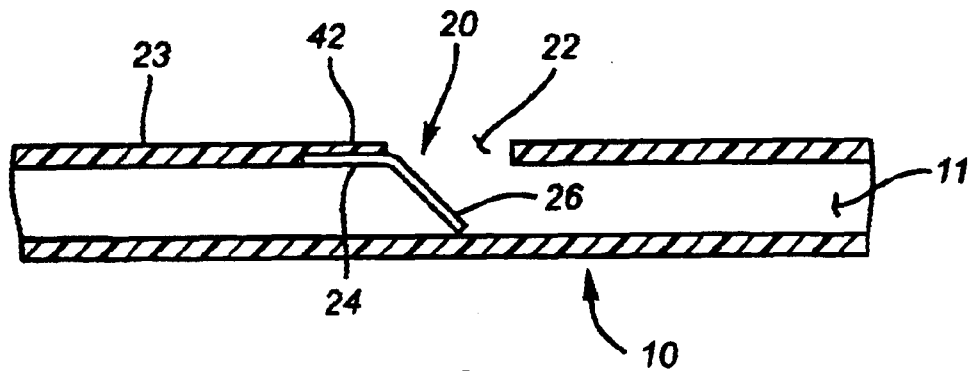
FIG. 5a is a partial side elevation view of the control valve and mounting seat according to the embodiment of FIG. 1.

In the first preferred embodiment, a catheter 10 has a distal end 12, a proximal end 14 with a hub 16 on the proximal end of the catheter, as shown in FIG. 1. The catheter 10 is a tubular member having a single lumen 11 running the length of the tubular member. A guidewire port 22 is adjacent to distal tip 18 of the catheter 10. A control valve 20 is located adjacent the guidewire port 22. Preferably, the control valve 20 and the guidewire port 22 are within 1 cm to 40 cm of the tip 18 of the catheter 10. More preferably, the control valve 20 and the guidewire port 22 are within 25 cm to 40 cm of the tip 18 of the catheter 10. However, the guidewire port 22 and control valve 20 may be as close to the distal tip 18 of the catheter 10 as desired.

The guidewire port 22 is an opening in the wall 23 of the catheter 10. The opening may be a hole or slit cut into the wall 23. The guidewire port 22 is preferably sized to allow passage of a guidewire 30 through the port 22, as shown in FIG. 2. Although the guidewire port 22 is generally sized to allow passage of a guidewire, the guidewire port 22 may be an opening sized to allow other devices to pass from the lumen 11 of the catheter 10 to the exterior of the catheter 10.

Figure 7:
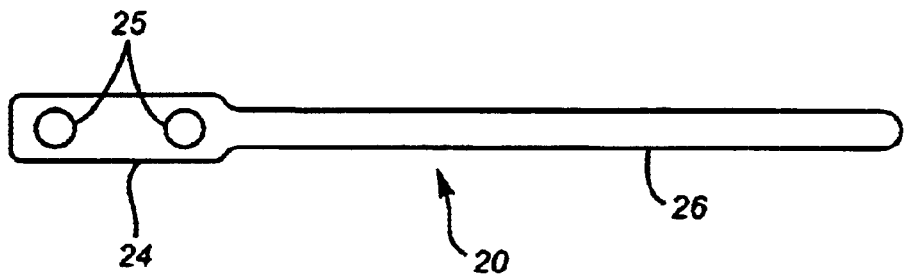
FIG. 7 is a plan view of the mounting piece and flexible gate of the control valve according to the embodiment of FIG. 1.

The control valve 20 preferably has a mounting piece 24 and a gate or finger 26 advantageously formed from a single piece of material, which is bent or hinged, as shown in FIGS. 7 and 8. The gate 26 extends inwardly into the lumen 11 of the catheter 10 when the mounting piece is mounted on the catheter wall 23. The mounting piece 24 and gate 26 are preferably formed of a thin, elastic material, such that the gate 26 can be pushed upward by a vaso-occlusive device without deforming. The gate 26 will then return to its downward position after the vaso-occlusive device has passed the gate 26. The mounting piece 24 and gate 26 are preferably Nitinol. However, any other suitable material may be used, such as shape memory polymers, Elgiloy or stainless steel. Alternative designs for the mounting piece 24 and gate 26 having two or more pieces may also be used. The gate 26 may be round, oval, rectangular or other shapes.

Figure 8A:
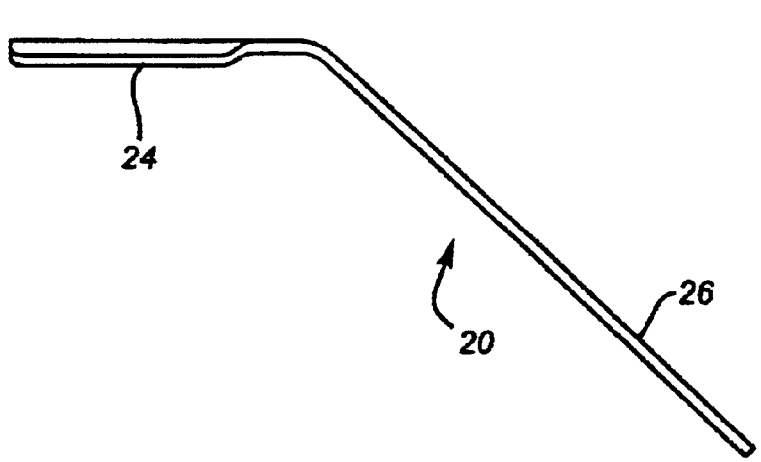
FIG. 8a is a side elevational view of the mounting piece and flexible gate of the control valve according to the embodiment of FIG. 1.
Figure 8B:
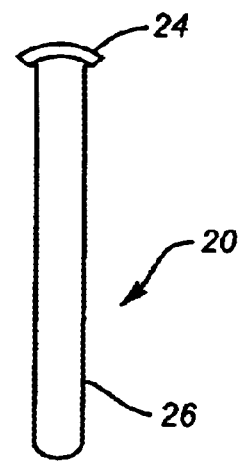
FIG. 8b is an end elevational view of the mounting piece and flexible gate of the control valve according to the embodiment of FIG. 1.

The mounting piece 24 is attached, preferably bonded to the inside of the wall 23, just next to the guidewire port 22. The mounting piece may be bonded to the wall 23 by placing the mounting piece 24 between two layers of polymer, with one of the layers of polymer in contact with the wall 23. The polymer layers are then melted, which bonds the mounting piece 24 to the wall 23. The mounting piece 24 preferably has two holes 25, such that when the layers of polymer are melted, the polymer fills the holes 25, which provides a stronger bond between the catheter wall 23 and the mounting piece 24. Other bonding methods may be used to attach the mounting piece 24 to the wall 23, such as using an adhesive. The wall 23 may be notched to form a seat 42 for the mounting piece 24, as shown in FIG. 5a. In this embodiment, the mounting piece 24 has a thickness, such that when seated, the mounting piece 24 will form a smooth interior surface in the lumen 11 of the catheter 10. Further, the mounting piece 24 is preferably curved, as shown in FIGS. 8a and 8b, to match the curved surface of the catheter wall 23. This prevents the vaso-occlusive device from catching on the mounting piece 24.

Figure 5B:
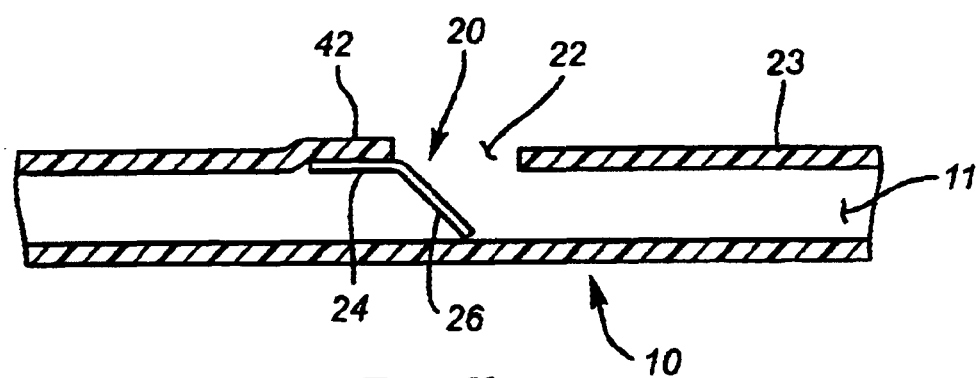
FIG. 5b is a partial side elevation view of the control valve and mounting seat according to an alternative embodiment of the control valve.

In a second preferred embodiment, the catheter wall 23 near the guidewire port 22 may be bent slightly outward to provide a seat 42 for the mounting piece 24, as shown in FIG. 5b. The wall is bent a sufficient distance, such that when the mounting piece 24 is mounted in the seat 42, the mounting piece 24 forms a smooth interior surface in the lumen 11 of the catheter 10.

Figure 6:
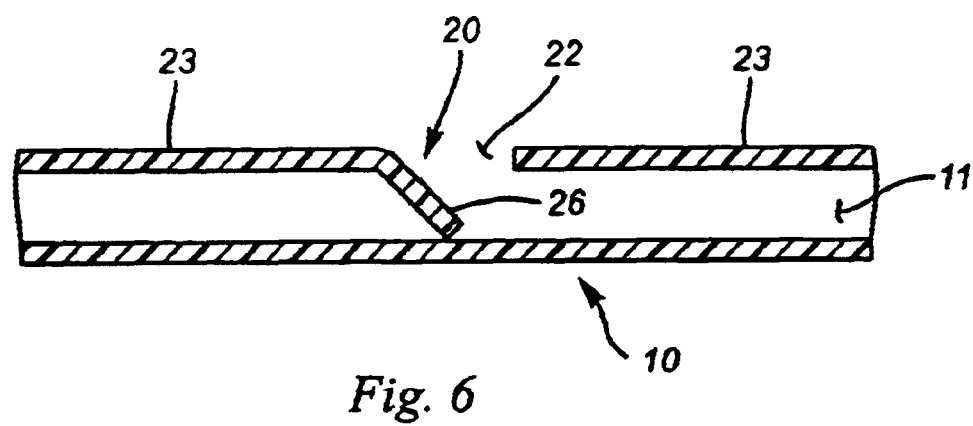
FIG. 6 is a partial side elevation view of the control valve according to an alternative embodiment of the catheter and control valve.

In a third preferred embodiment, the gate 26 is formed from the portion of the catheter wall that is cut to form the guidewire port 22. Only a portion of the catheter wall is cut to form a gate 26. The proximal side of the gate 26 remains connected to the catheter wall 23, as shown in FIG. 6. The gate 26 is then bent or hinged downward into the lumen 11 of the catheter 10, opening the guidewire port 22. In this way, the gate 26 is integral to the catheter wall and no bonding of a separate valve piece is necessary. As in the first and second embodiments, as the vaso-occlusive device is pushed through the lumen 11 of the catheter 10, the gate 26 is forced upward closing the guidewire port 22, allowing the vaso-occlusive device to pass the gate 26. Once the vaso-occlusive device is past the guidewire port 22 and gate 26, the gate 26 will return to its original bent position, closing the lumen 11 of the catheter.

In the preferred embodiments described above, the control valve 20, acts as a check valve, preventing passage of a device through the lumen 11 of the catheter 10 in one direction, while allowing passage of a device through the lumen 11 in the opposite direction, as shown in FIGS. 2 and 4. As the catheter 10 is loaded onto the guidewire 30, the guidewire is directed out of the lumen 11 of the catheter 10 by the control valve 20. The gate 26, normally in a closed position, prevents the guidewire from further passage through the lumen 11. Preferably, the gate 26, in a closed position, will seat in the lumen 11 of the catheter 10 at an angle, such that when the guidewire 30 is pushed against the gate 26, the guidewire 30 is directed toward the guidewire port 22 and out of the lumen 11 of the catheter 10. Thus, only a small portion of the distal end 12 of the catheter 10 is over the guidewire 30. Further, the seating angle of the gate 26 is such that the gate 26 is always in contact with the inner surface of the wall 23 of the catheter 10 while the catheter 10 is loaded onto the guidewire 30.

When the catheter 10 is loaded with a vaso-occlusive device, such as a coil, the gate 26 is initially in the closed position, as shown in FIG. 3. As the vaso-occlusive device reaches the control valve 20, the end of the vaso-occlusive device pushes against the gate 26, forcing the gate toward the guidewire port 22. As the gate 26 is forced toward the guidewire port 22, it closes the port 22 and opens the lumen 11, which prevents the vaso-occlusive device from exiting through the port 22, as shown in FIG. 4. Thus, the vaso-occlusive device will continue down the length of the catheter 10 and out the distal tip 18, into the desired vasculature site. Once the vaso-occlusive device has been delivered, the gate 26 will return to its closed position.

Thus, while the preferred embodiments have been shown and described, many changes and modifications may be made thereunto without the departing from the spirit and scope of the invention. The invention, therefore, should not be limited, except by the following claims, and their equivalents.

What is claimed is:

1. A catheter, comprising:
    a flexible tubular member having a proximal end and a distal end with a lumen extending within the tubular member, the tubular member having an opening adjacent the distal end, the opening extending through the wall of the tubular member; and
    a control valve adjacent the opening and operable in association with the opening, the control valve moveable between a first position and a second position;
    wherein the control valve comprises a mounting piece, and a gate.

2. The catheter of claim 1, wherein the mounting piece is bonded to the tubular member.

3. A catheter, comprising:
    a flexible tubular member having a proximal end, a distal end, and a lumen extending between the proximal and the distal ends, the tubular member having a guidewire port located proximal to the distal end of the tubular member; and
    a guidewire valve disposed on the tubular member proximal to the guidewire port, the guidewire valve directing a guidewire out of the lumen of the tubular member while allowing passage of a device through the lumen of the tubular member and out the distal end of the tubular member.

4. The catheter of claim 3, wherein the guidewire port is from 1 cm and 40 cm away from the distal end of the tubular member.

5. The catheter of claim 3, wherein the guidewire port is sized to allow passage of a guidewire through the port.

6. The catheter of claim 3, wherein the guidewire port extends through a wall of the flexible tubular member.

7. The catheter of claim 3, wherein the guidewire valve comprises a gate secured adjacent to the guidewire port.

8. The catheter of claim 7, wherein the gate is operable in the first position to direct a guidewire out of the lumen of the tubular member through the guidewire port, and a second position to prevent an object within the lumen of the tubular member from escaping through the guidewire port.

9. The catheter of claim 8, wherein movement of the device through the lumen forces the gate into the second position.

10. The catheter of claim 7, wherein the gate is operable in the first position to direct a guidewire out of the lumen of the tubular member through the guidewire port in a proximal direction, and a second position to prevent an object within the lumen of the tubular member from escaping through the guidewire port in a distal direction.

11. A catheter comprising:
 a flexible tubular member having a proximal end and a distal end with a lumen extending within the tubular member, the tubular member having an opening adjacent the distal end, the opening extending through the wall of the tubular member; and
 a control valve adjacent the opening and operable in association with the opening, the control valve moveable between a first position and a second position;
 wherein the control valve comprises a gate secured adjacent to the opening.

12. The catheter of claim 11, wherein the gate is operable in the first position to direct a guidewire out of the lumen of the tubular member through the opening, and a second position to prevent an object within the lumen of the tubular member from escaping through the opening.

13. The catheter of claim 12, wherein movement of the device through the lumen forces the gate into the second position.

14. The catheter of claim 11, wherein the gate is operable in the first position to direct a guidewire out of the lumen of the tubular member through the opening in a proximal direction, and a second position to prevent an object within the lumen of the tubular member from escaping through the opening in a distal direction.

15. The catheter of claim 11, wherein the opening is from 1 cm to 40 cm away from the distal end of the tubular member.

16. The catheter of claim 11, wherein a proximal side of the gate is integrally connected to the wall of the tubular member.

17. A catheter, comprising:
 a flexible tubular member having a proximal end, a distal end, and a lumen extending between the proximal end distal ends, the tubular member having a port located proximal the distal end of the tubular member, the port being in communication with the lumen; and
 a valve disposed on the tubular member proximal to the port, the valve operable in association with the port, the valve having a gate that is moveable between a first and second position;
 wherein when the gate is in the first position, the gate is capable of directing a guidewire out of the lumen of the tubular member through the port, and when the gate is in the second position, the gate prevents an object within the lumen of the tubular member from escaping through the port.

18. The catheter of claim 17, wherein movement of the device through the lumen forces the gate into the second position.

19. The catheter of claim 17, wherein the port is located a distance of 1 cm to 40 cm from the distal end of the tubular member.

20. The catheter of claim 17, wherein the port extends through a side wall of the tubular member.

21. The catheter of claim 17, wherein the gate is capable of directing the guidewire through the opening in a proximal direction, and prevents the object from escaping through the opening in a distal direction.

* * * * *